United States Patent [19]

Imran

[11] Patent Number: 5,389,073
[45] Date of Patent: Feb. 14, 1995

[54] STEERABLE CATHETER WITH ADJUSTABLE BEND LOCATION

[75] Inventor: Mir A. Imran, Palo Alto, Calif.

[73] Assignee: Cardiac Pathways Corporation, Sunnyvale, Calif.

[21] Appl. No.: 134,487

[22] Filed: Oct. 12, 1993

Related U.S. Application Data

[63] Continuation of Ser. No. 983,962, Dec. 1, 1992, abandoned.

[51] Int. Cl.⁶ .............................................. A61M 37/00
[52] U.S. Cl. ..................................... 604/95; 128/658; 128/772; 604/281
[58] Field of Search ................... 604/95, 281; 128/772, 128/656, 658, 45 M

[56] References Cited

U.S. PATENT DOCUMENTS

| | | | |
|---|---|---|---|
| 3,674,014 | 7/1972 | Tillander | 604/95 |
| 3,773,034 | 11/1973 | Burns et al. | 604/95 |
| 5,090,956 | 2/1992 | McCoy | 128/772 |
| 5,114,402 | 5/1992 | McCoy | 604/95 |

FOREIGN PATENT DOCUMENTS

WO9111213 8/1991 WIPO.

Primary Examiner—Jerome L. Kruter
Attorney, Agent, or Firm—Flehr, Hohbach, Test Albritton & Herbert

[57] ABSTRACT

Steerable catheter having an adjustable bend location comprising a flexible elongate tubular member having proximal and distal extremities. A plurality of circumferentially spaced-apart flexible elements are disposed in the distal extremity for causing bending of the distal extremity of the flexible elongate member. A bend positioner is disposed at the distal extremity of the flexible elongate member for selecting the location in the distal extremity of the flexible elongate tubular member where bending is to occur to thereby adjust the length of the flexible elongate member which extends beyond the bend.

10 Claims, 2 Drawing Sheets

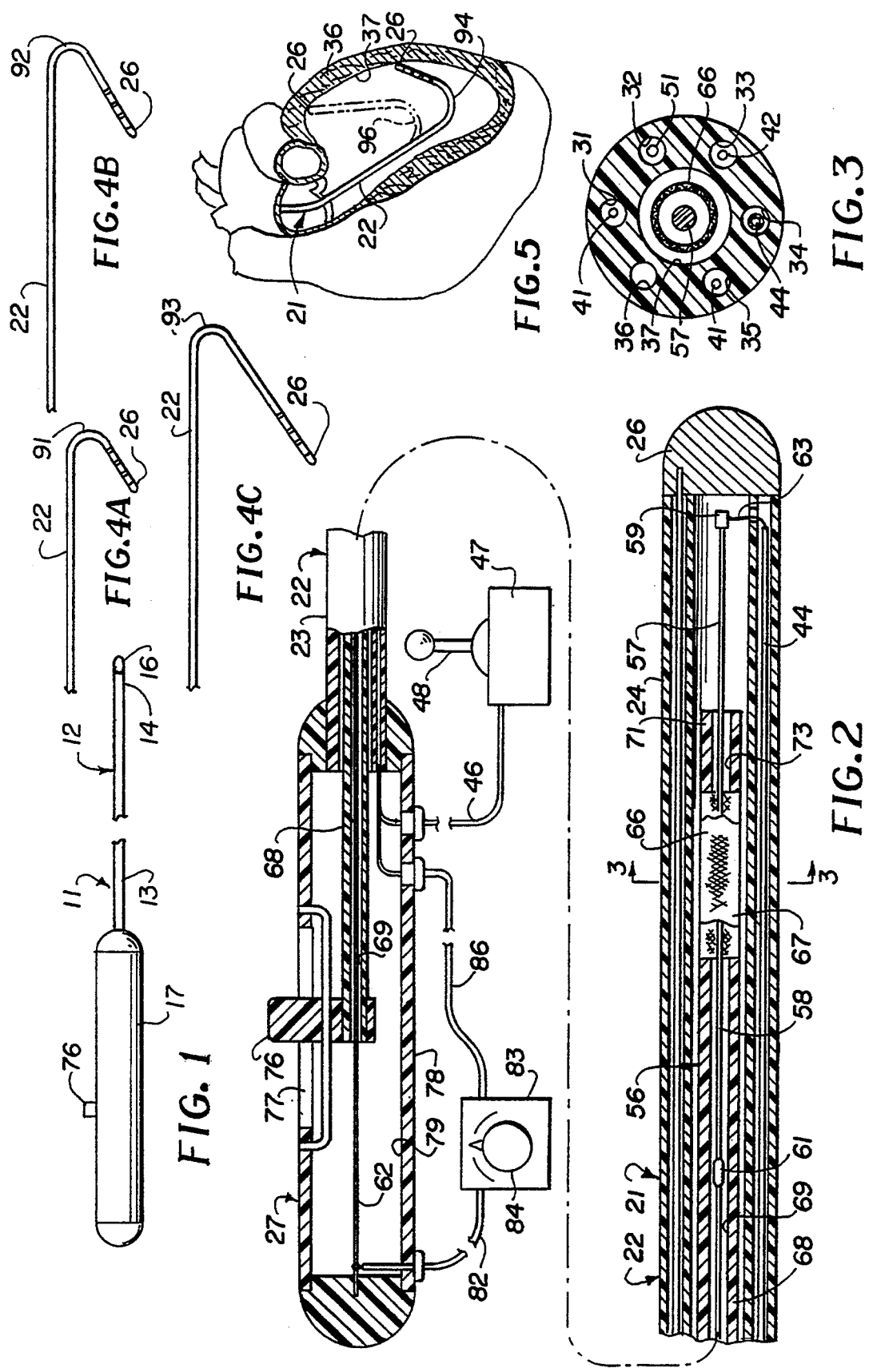

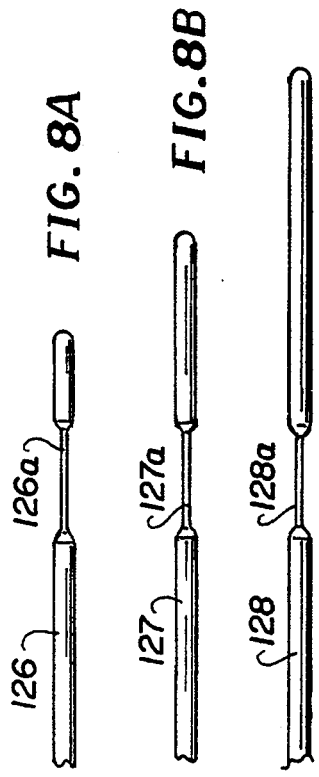
FIG. 6
FIG. 7
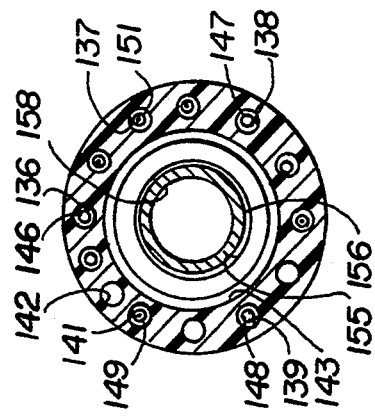
FIG. 8A
FIG. 8B
FIG. 8C
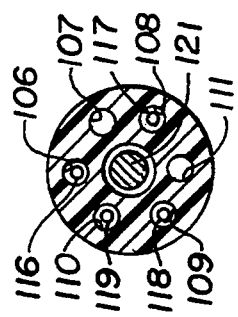
FIG. 10
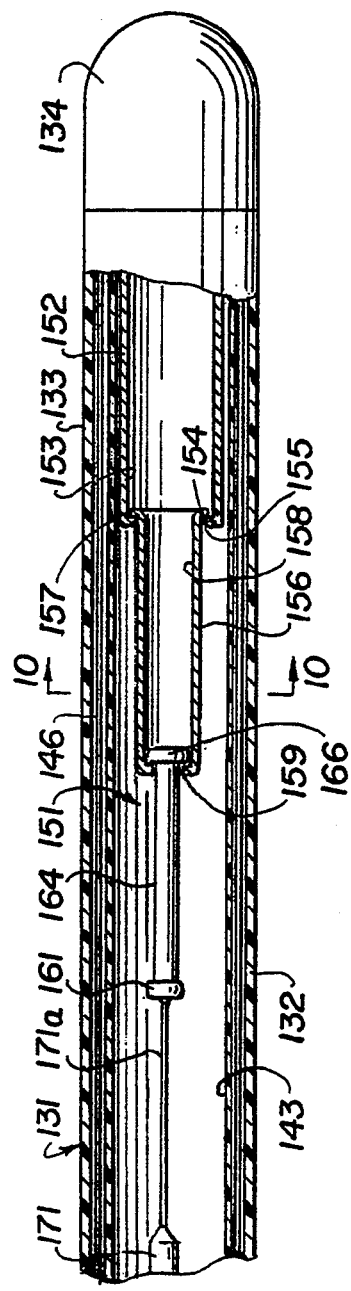
FIG. 9

STEERABLE CATHETER WITH ADJUSTABLE BEND LOCATION

This is a continuation of application Ser. No. 07/983,962, filed Dec. 1, 1992, now abandoned.

This invention relates to a steerable catheter with an adjustable bend location and method.

In certain procedures, as for example ablation procedures for use with a steerable catheter in the human heart, it has been found that it is difficult to provide a bend in the appropriate location in the distal extremity of the steerable catheter while maintaining the rigidity of the distal extremity. This has found to be particularly true in patients having large hearts. There is therefore a need for a new and improved steerable catheter which overcomes these difficulties.

In general, it is an object of the present invention to provide a steerable catheter with an adjustable bend location and method.

Another object of the invention is to provide a catheter and method of the above character which can be utilized with different types of bending mechanisms for the distal extremity of the catheter.

Another object of the invention is to provide a catheter and method of the above character in which the adjustment of the bend location can be readily accomplished.

Additional objects and features of the invention will appear from the following description in which the preferred embodiments are set forth in detail in conjunction with the accompanying drawings.

FIG. 1 is a side elevational view of a steerable catheter incorporating the present invention.

FIG. 2 is a side elevational view partially in cross-section showing one embodiment of a steerable catheter incorporating the present invention utilizing a shape-memory element.

FIG. 3 is a cross-sectional view taken along the line 3—3 of FIG. 2.

FIGS. 4A, 4B and 4C show four examples of how an adjustable bend location in the steerable catheter makes possible bends in different locations in the distal extremity of the catheter.

FIG. 5 is a diagrammatic illustration showing the manner in which the steerable catheter of the present invention can be utilized in a human heart to provide a different bend location to make it possible to reach difficult-to-reach portions of the wall forming a chamber in the heart.

FIG. 6 is a partial cross-sectional view of another embodiment of a steerable catheter incorporating the present invention utilizing removable stiffening elements having weakened portions at different longitudinal positions of the stiffening elements.

FIG. 7 is a cross-sectional view taken along the line 7—7 of FIG. 6.

FIGS. 8A, 8B and 8C show stiffening elements having weakened regions in different longitudinal portions of the stiffening element.

FIG. 9 is a partial cross-sectional view of the distal extremity of another embodiment of a steerable catheter incorporating the present invention utilizing telescoping stiffening elements.

FIG. 10 is a cross-sectional view taken along the line 10—10 of FIG. 9.

In general, the steerable catheter of the present invention consists of a flexible elongate tubular member having proximal and distal extremities. A plurality of circumferentially spaced-apart flexible elements are disposed in the distal extremity for causing bending of the distal extremity of the flexible elongate member. Movable means is disposed in the distal extremity of the flexible elongate member for selecting the location where bending in the distal extremity will take place.

More in particular, the steerable catheter 11 incorporating the present invention consists of a flexible elongate member 12 formed of a suitable material such as plastic which is provided with proximal and distal extremities 13 and 14. An ablation electrode 16 is carried by the distal extremity 14. A hand-held control mechanism 17 is mounted on the proximal extremity 13. The hand-held control mechanism 17 can be of various types. For example it can be of the type which can be utilized for actuating pull wires (not shown) extending longitudinally of the flexible elongate tubular member 12 which are well known to those skilled in the art and which can be utilized for bending the distal extremity of the flexible elongate tubular member 12. Alternatively, it can be provided with means for controlling flexible elongate elements having a negative coefficient of expansion disposed in the distal extremity 14 of the flexible elongate tubular member 12 as described in co-pending application Ser. No. 07/793,858, filed Nov. 18, 1991. Means not shown in FIG. 1 is provided for adjusting the bend location in the distal extremity of the flexible elongate tubular member 12 which will hereinafter be described in conjunction with specific embodiments of the present invention.

In FIGS. 2 and 3 there is disclosed a steerable catheter 21 which consists of a flexible elongate tubular member 22 which is provided with proximal and distal extremities 23 and 24. A metal ablation electrode 26 is secured to the distal extremity 24. A hand-held control mechanism 27 is mounted on the proximal extremity 23 of the flexible elongate tubular member 22. The flexible elongate tubular member 22 is formed of a suitable material such as plastic and is provided with a plurality of circumferentially spaced-apart lumens 31-36, and a central lumen 37, all of which extend the length of the flexible elongate tubular member 22. A plurality of flexible elongate elements, as for example three of such elements 41, 42 and 43, are disposed 120° apart and are provided in the lumens 31, 33 and 35. These flexible elongate elements 41, 42 and 43 are disposed in the distal extremity 24 of the flexible elongate tubular member 22 and are formed of a material which has a negative coefficient of expansion. The distal extremities of these flexible elongate members 41, 42 and 43 are connected to a common ground return 44 provided in the lumen 34. The three flexible elongate elements 41, 42 and 43 are also connected to conductors (not shown) which extend to the proximal extremity 23 of the flexible elongate member and with the ground return 44 connected into a cable 46 extending from the control mechanism 17 and are connected to a joystick control console 47 of the type described in co-pending application Ser. No. 07/793,858, filed Nov. 18, 1991, and which includes a joystick 48. The ablation electrode 26 is connected by a conductor 51 provided in the lumen 32 and extending into the control mechanism 17 and is connected to a suitable ablation power supply (not shown) conventionally used with such catheters.

Bend location adjustment means 56 is provided in the distal extremity 24 of the flexible elongate tubular member 22 and consists of a shape-memory element 57 formed of a suitable material such as Nitinol which has been provided with a memory which makes it assume a straight condition when it is heated such as by the application of electrical energy thereto. The shape-memory element 57 is provided with proximal and distal extremities 58 and 59. The proximal extremity 58 is connected by a joint 61 to a conductor 62 which extends into the control mechanism and is connected as hereinafter described. The distal extremity 59 is connected to a ground return conductor 44 by wire 63. The shape-memory element 57 can have a suitable diameter, as for example 5–20 mils. The bend adjustment means 56 also includes selective conductive bypass means 66 which is movable longitudinally along the length of the shape-memory element 57 to selectively inhibit current flow in a portion of the shape-memory element to permit bending of the shape-memory element 57 in that portion of the shape-memory element.

The conductive bypass means 66 as shown in FIGS. 2 and 3 consists of an elongate cylindrical sleeve 67 formed of a suitable conducting material, as for example a silver mesh or braid, through which the shape-memory element 57 extends. Means is provided for adjusting the sleeve 67 longitudinally over the shape-memory element 57 and consists of a flexible tubular member 68 formed of a suitable insulating material such as plastic which is slidably mounted in the central lumen 37. The tubular member 68 is provided with a bore 69 therein extending the length thereof and in which the shape-memory element 57 is disposed. As can be seen particularly in FIG. 2, the sleeve 67 has one end secured to the distal extremity of the flexible tubular member 68. The other end of the sleeve 67 is supported by another tubular member 71 of the same material and of the same diameter as the flexible tubular member 68 and is provided with a bore 72 through which the shape-memory element 57 extends. The sleeve 67 can be affixed to the tubular members 68 and 71 by suitable means such as an adhesive.

In order to ensure good conductivity between the silver braid or mesh sleeve 67, the shape-memory element should be cleaned with nitric and hydrochloric acids to remove any oxidation which may be present on the shape-memory element 57. This ensures that there is good electrical contact between the sleeve 67 and the shape-memory element so that minimal or no current flows in the portion of the shape-memory element 57 which is covered by the sleeve.

Means is provided for controlling the movement of the flexible tubular member 68 and the sleeve 67 carried thereby from the control mechanism 27 and consists of a control member 76 which is secured to the proximal extremity of the tubular member 68. The control member 73 extends diametrically of the tubular member 68 through a longitudinally extending slot 77 provided in the sidewall of a cylindrical housing 78. The cylindrical housing 78 can be formed of a suitable material such as plastic or metal, and is sized in such a manner so that it is adapted to be held by the human hand. For example, it can have a diameter of approximately 1″ and a length of 5–6″. It is provided with a cylindrical recess 79 therein permitting the control member 76 with the attached flexible tubular member 68 to move therein relative to the conductor 62 which is mounted in an end cap 81 secured to the proximal extremity of the housing 78. The conductor 62 is connected to a cable 82 which extends out of the housing 78 and is connected to a variable current power supply 83 which is provided with a control knob 84 to adjust the amount of current which is supplied to the sleeve 67. The variable current power supply 83 is also provided with another cable 86 which is connected to the ground return conductor 44.

Operation and use of the steerable catheter 21 may now be briefly described as follows. Let it be assumed that it is desired to form a bend in the distal extremities 24 of the flexible elongate tubular member 22 in the position where the sleeve 67 has been located by movement of the control member 76. Current is supplied under the control of the control knob 84 from the variable current power supply 83 to the shape-memory element 57. The shape-memory element 57, when it is supplied with electrical energy, attempts to return to its memorized condition which, as pointed out before, is a straight condition. At the same time, it becomes stiffer. The conductive sleeve 67 however permits the portion of the shape-memory element 57 covered by the sleeve to remain flexible. This occurs because the sleeve 67, which is in close intimate contact with the shape-memory element 57, serves as a current bypass or bridge and causes the current to flow through the highly conductive silver mesh sleeve 67 to thereby bridge that portion of the shape-memory element 57 covered thereby so that it remains relatively flexible. Thus, the portion of the shape-memory element 57 underlying or within the sleeve 67 does not heat up and remains flexible and does not attempt to assume the straight condition of the remainder of the shape-memory element 57. By adjusting the longitudinal position of the sleeve with respect to the shape-memory element 57, it is possible to adjust the location at which the shape-memory element 57 will be flexible to permit bending at different locations so that shorter or longer straight or stiff portions can be provided at the distal extremity of the catheter 11 beyond the bend. Examples of such different locations of bends is shown by the bends 91, 92 and 93 in FIGS. 4A, 4B and 4C, respectively which show progressively longer stiff portions extending distally beyond the bends.

FIG. 5 shows by providing different bend locations for the steerable catheter 11, it is possible to reach difficult-to-reach positions in the human heart. Two different bends represented by the bends 94 and 96 in the catheter 11 are shown in which the bend 96 in contradistinction to the bend 94 makes it possible to reach a difficult-to-reach area of the wall 96 forming the chamber 97 of the human heart 98.

Another embodiment of a steerable catheter incorporating the present invention is shown in the catheter 101 in FIGS. 6 and 7 which consists of a flexible elongate tubular member 102 formed of a suitable material such as plastic which is provided with a distal extremity 103 having a metal electrode 104 provided thereon. The flexible elongate member 102 is provided with a plurality of circumferentially spaced-apart lumens 106–111 and a central lumen 112. At least three pull wires 116, 117 and 118 are provided in the lumens 106, 108 and 109, which are connected into the distal extremity and which extend to the proximal end of the catheter 101 and are controlled by a conventional control mechanism (not shown) for causing bending of the distal extremity of the tubular elongate member 102. A conductor 119 is provided in the lumen 110 and is connected to the electrode 104. An elongate stiffening element 121 is slidably mounted in the central lumen 112. This stiffening element 121 is provided with a weakened longitudinal portion 121a of the stiffening element 121. This weakened portion 121a can be of a suitable length, as for example 1–5 cm. It can be seen that by utilizing such a stiffening element with such a weakened portion that the bending of the distal extremity 103 of the flexible elongate tubular member 102 will occur in the region of the weakened portion 121a.

In the event that it is desirable to provide a bend which has a longer stiffer portion extending beyond the bend, the stiffener element 121 can be interchanged with other stiffener elements, as for example stiffener elements 126, 127 and 128, as shown in FIGS. 8A, 8B and 8C, having weakened longitudinal portions 126a, 127a and 128a, respectively, at different longitudinal positions of the stiffener elements 126, 127 and 128. It can be seen that by selecting an appropriate stiffener element that the bend in the distal extremity of the flexible elongate member 102 can be made to occur in the desired location to provide different hinge points and also to provide different lengths of the stiffener element extending beyond the weakened region or hinge point.

Another embodiment of a steerable catheter incorporating the present invention is shown in the steerable catheter 131 depicted in FIGS. 9 and 10. As shown therein, the catheter 131 consists of a flexible elongate member 132 formed of a suitable material such as plastic which is provided with a distal extremity 133 to which there is secured a tip electrode 134. The flexible elongate member 132 is provided with a plurality of circumferentially spaced-apart lumens 137–142 and a central lumen 143. At least three flexible elongate elements 146, 147 and 148 are disposed in the lumens 136, 138 and 139 and are formed of a material having a negative coefficient of expansion. Their distal extremities are connected to a common ground return conductor 149 provided in the lumen 141. A conductor 151 is provided in the lumen 137 and is connected to the electrode 134. The flexible elongate elements 146, 147 and 148 are connected to a joystick-type of control hereinbefore described in connection with the embodiment as shown in FIG. 2, and for that reason is not shown in FIGS. 9 and 10.

The means for adjusting the bend location for the bending of the distal extremity 133 of the flexible elongate tubular member 132 is in the form of a telescoping assembly 151 formed of a suitable material such as stainless steel mounted in the central lumen of the distal extremity 133 of the catheter 131. The telescoping assembly 151 is movable between collapsed and extended positions and consists of an outer cylindrical member 152 which is secured within the distal extremity 133 by suitable means such as an adhesive. The outer cylindrical member is provided with a cylindrical bore 153 and a swaged end 154 providing an opening 155 in communication with the bore 153. An intermediate cylindrical member 156 is slidably mounted within the outer cylindrical member 152 and is provided with a flanged end 157 which is adapted to engage the swaged end 154 of the outer cylindrical member 152. The intermediate cylindrical member 156 is provided with a bore 158 and has a swaged end 159 forming a hole 161 extending therethrough. An inner cylindrical member 164 is provided which has a flange 166 which is adapted to travel in the bore 158. The inner cylindrical member 164 travels through the hole 161 and forms the distal extremity of an elongate flexible push-pull element 171 which extends to the proximal extremity (not shown) of the flexible elongate member 132. The flexible elongate element 171 can be formed of a suitable material such as stainless steel and can have a diameter of 0.012–0.025". It is provided a portion 171a of reduced diameter in close proximity to the inner cylindrical member 164 as shown in FIG. 9. By way of example, it can have a reduced diameter ranging from 0.006" to 0.015". The diameter of the flexible elongate element 171 should be of a diameter which is slightly greater than the size of the hole 161 for a purpose hereinafter described.

In utilizing the steerable catheter 131 shown in FIG. 9, the hinge point or bend location for the distal extremity 133 of the flexible elongate element 132 can be readily adjusted. For example, for the shortest possible stiff or straight length extending beyond the bend, the telescoping assembly 151 is in a collapsed position in which the push-pull element 171 has been pushed towards the distal extremity so that the distal extremity of the flexible elongate member 171 is in engagement with the proximal extremity of the intermediate cylindrical member 156 and the intermediate cylindrical member is disposed entirely within the outer cylindrical member 132. To increase the length of this stiff portion extending beyond the bend, it is merely necessary to withdraw proximally the flexible elongate element 171 which will first pull the inner cylindrical member 164 proximally to increase the length of the stiff portion extending beyond the bend provided by the region 171a. To provide a still longer stiff portion extending beyond the bend, it is merely necessary to pull proximally the flexible elongate member 171 to cause the intermediate cylindrical member 156 to be pulled out of the outer cylindrical member 152 to thereby increase the length of the telescoping assembly 151 and to also increase the length of the stiff portion extending beyond the bend or hinge point 171a. Thus, it can be seen that by use of the telescoping assembly 151 and by pushing or pulling on the flexible elongate element 171 it is possible to adjust the length of the telescoping assembly and to thereby adjust the length of the stiff portion extending beyond the bend.

From the foregoing it can be seen that there have been provided a number of different embodiments of an invention in which it is possible to adjust the bend location in the distal extremity of a steerable catheter which makes it possible for the steerable catheter to be utilized to move its tip into many different locations, and particularly into locations which are difficult to reach with conventional steerable catheters. This is particularly advantageous in ablation procedures where it is desired to precisely locate the ablation electrode for performing an ablation procedure.

What is claimed is:

1. In a steerable catheter having a continuously adjustable bend location along the distal axial length thereof, a flexible elongate tubular member having proximal and distal extremities, a control mechanism secured to the proximal extremity, a plurality of circumferentially spaced-apart flexible elements disposed in the distal extremity for causing bending of the distal extremity of the flexible elongate member and movable means controlled by the control mechanism disposed at the distal extremity of the flexible elongate member for selecting the location in the distal extremity where bending is to occur to thereby adjust the length of the flexible elongate member which extends beyond the bend, said movable means being in the form of a shape-memory element having a memory which makes it assume a straight position upon the application of an electrical current thereto and bypass means adjustable longitudinally of the shape-memory element for causing the current applied to the shape-memory element to bypass a portion of the length of the shape-memory element so that it remains flexible at that portion to provide a hinge point for the bend.

2. In a steerable catheter having an adjustable bend location, a flexible elongate tubular member having proximal and distal extremities, a plurality of circumferentially spaced-apart flexible elements disposed in the distal extremity for causing bending of the distal extremity of the flexible elongate member and movable means adjustably disposed at the distal extremity of the flexible elongate member for selecting while the steerable catheter is use the location in the distal extremity where bending is to occur to thereby adjust the length of the flexible elongate member which extends beyond the bend, said movable means being in the form of a shape-memory element having a memory which makes it assume a straight position upon the application of an electrical current thereto and bypass means adjustable longitudinally of the shape-memory element for causing the current applied to the shape-memory element to bypass a portion of the length of the shape-memory element so that it remains flexible at that portion to provide a hinge point for the bend, said bypass means consisting of a conductive sleeve movable longitudinally of the shape-memory element.

3. A catheter as in claim 2 wherein said sleeve is in the form of conductive mesh of a highly conductive material.

4. A catheter as in claim 2 together with means coupled to said sleeve for moving said sleeve longitudinally of said shape-memory element, said means coupled to the sleeve extending to the proximal extremity of the flexible elongate member.

5. A catheter as in claim 4 together with a control mechanism mounted on the proximal extremity of the flexible elongate member, said control mechanism including a control member movable longitudinally thereof and connected to the member coupled to the sleeve.

6. A catheter as in claim 4 wherein said means coupled to said sleeve is in the form of a tubular member having a bore therein and wherein said shape-memory element extends through said bore.

7. In a steerable catheter having an adjustable bend location, a flexible elongate tubular member having proximal and distal extremities, a plurality of circumferentially spaced-apart flexible elements disposed in the distal extremity for causing bending of the distal extremity of the flexible elongate member and removable means disposed at the distal extremity of the flexible elongate member for selecting while the steerable catheter is in use in the body of a patient the location in the distal extremity where bending is to occur to thereby adjust the length of the flexible elongate member which extends beyond the bend, said removable means being a selected one of a plurality of stiffening elements, each stiffening element having a weakened region providing a hinge point in a different longitudinal position of the stiffening element than the longitudinal positions of the other of said stiffening elements.

8. A catheter as in claim 7 wherein said stiffening element is comprised of an elongate flexible member of a predetermined cross-section and wherein said weakened region is formed by producing a region of reduced cross-section.

9. In a steerable catheter having an adjustable bend location, a flexible elongate tubular member having proximal and distal extremities, a control mechanism secured to the proximal extremity, a plurality of circumferentially spaced-apart flexible elements disposed in the distal extremity of the flexible elongate tubular member for causing bending of the distal extremity of the flexible elongate member and movable means controlled by the control mechanism disposed at the distal extremity of the flexible elongate member for selecting while the steerable catheter is in use the location in the distal extremity where bending is to occur to thereby adjust the length of the flexible elongate member which extends beyond the bend, said movable means being in the form of a telescoping assembly movable between collapsed and extended positions and comprising at least first and second telescoping members telescopically mounted with respect to each other disposed in the distal extremity of the flexible elongate member, flexible elongate means extending to the proximal extremity of the flexible elongate member and coupled to said second telescoping member of said telescoping assembly for moving said telescoping assembly between said collapsed and extended positions, said flexible elongate means coupled to said telescoping assembly including a weakened longitudinal portion which forms a hinge point.

10. A steerable catheter having an adjustable bend location, a flexible elongate tubular member having proximal and distal extremities, a plurality of stiffening elements, one of said stiffening elements being disposed in said elongate tubular member and having a weakened region providing a hinge point different from the hinge points of the other of said stiffening elements, said other of the stiffening elements having weakened regions providing hinge points in different longitudinal positions of the stiffening element whereby when different stiffening elements are inserted into the flexible elongate tubular member, the distal extremity of the flexible elongate tubular member has a different hinge point.

* * * * *